United States Patent
Goodbread et al.

(10) Patent No.: US 10,502,670 B2
(45) Date of Patent: Dec. 10, 2019

(54) TEMPERATURE COMPENSATED DENSITY VISCOSITY SENSOR HAVING A RESONANT SENSING ELEMENT

(71) Applicant: RHEONICS GMBH, Winterthur (CH)

(72) Inventors: Joseph H. Goodbread, Winterthur (CH); Sunil Kumar, Winterthur (CH); Klaus Haeusler, Zurich (CH); Bernhard Zybach, Zurich (CH)

(73) Assignee: RHEONICS, GMBH, Winterthur (CH)

( * ) Notice: Subject to any disclaimer, the term of this patent is extended or adjusted under 35 U.S.C. 154(b) by 160 days.

(21) Appl. No.: 15/566,675

(22) PCT Filed: Apr. 14, 2016

(86) PCT No.: PCT/IB2016/000766
§ 371 (c)(1),
(2) Date: Oct. 13, 2017

(87) PCT Pub. No.: WO2016/166610
PCT Pub. Date: Oct. 20, 2016

(65) Prior Publication Data
US 2019/0003947 A1    Jan. 3, 2019

Related U.S. Application Data

(60) Provisional application No. 62/147,180, filed on Apr. 14, 2015.

(51) Int. Cl.
*G01N 9/00* (2006.01)
*G01N 11/16* (2006.01)
(Continued)

(52) U.S. Cl.
CPC ............. *G01N 9/002* (2013.01); *G01N 11/10* (2013.01); *G01N 11/16* (2013.01); *G01N 11/162* (2013.01);
(Continued)

(58) Field of Classification Search
CPC ................ G01N 11/16; G01N 11/162; G01N 2291/02818; G01N 9/002; G01N 2009/006; G01N 29/036; G01N 11/10
See application file for complete search history.

(56) References Cited

U.S. PATENT DOCUMENTS 2,839,915 A * 6/1958 Rich ...................... G01N 11/16
                                                        73/54.25
3,382,706 A * 5/1968 Fitzgerald ............ G01N 11/162
                                                        73/54.25
(Continued)

FOREIGN PATENT DOCUMENTS

EP       2045594 A1    4/2009
GB        763875 A  * 12/1956 ............. G01N 11/14
(Continued)

OTHER PUBLICATIONS

RS5000 Series Drives and Rheometers, Rheometer Services, Inc., available on the internet at <https://web.archive.org/web/20131210143950/http://www.rheometerservices.com/products/rs5000a.html, Dec. 10, 2013. (Year: 2013).*

*Primary Examiner* — David A Rogers
(74) *Attorney, Agent, or Firm* — Timothy E. Siegel Patent Law, PLLC; Timothy E. Siegel (57) ABSTRACT

A fluid density measurement device that includes a housing, defining a chamber and an aperture; a resonator having length that is at least 5 times greater than its smallest diameter and having a longitudinal axis and a nodal plane, transverse to the longitudinal axis. The resonator further includes a tube having a first end and a second end; a second-end closure, closing the second end; and a drive rod centrally attached to the second-end closure and extending to the tube first end. Further, the device includes a resonator transducer assembly and the resonator is sealingly joined to the aperture at the nodal plane, so that an enclosed portion (Continued)

extends into the chamber and an exposed portion extends outside of the chamber, and wherein the chamber tends to assume the temperature of the exposed resonator portion, causing the resonator to be isothermal.

18 Claims, 11 Drawing Sheets

(51) Int. Cl.
    *G01N 29/036*     (2006.01)
    *G01N 11/10*     (2006.01)

(52) U.S. Cl.
    CPC ..... *G01N 29/036* (2013.01); *G01N 2009/006* (2013.01); *G01N 2291/02818* (2013.01)

(56) References Cited

U.S. PATENT DOCUMENTS

| | | | | |
|---|---|---|---|---|
| 3,559,464 A * | 2/1971 | Foust et al. | ............ | G01N 11/08 73/54.06 |
| 4,129,031 A * | 12/1978 | Tehon | ............ | G01N 9/002 73/32 A |
| 4,566,181 A * | 1/1986 | Matusik | ............ | G01N 11/162 29/602.1 |
| 4,644,803 A * | 2/1987 | Ward | ............ | G01N 9/002 177/208 |
| 4,704,898 A * | 11/1987 | Thone | ............ | G01N 11/16 73/54.25 |
| 4,728,698 A * | 3/1988 | Isayev | ............ | C08L 69/00 264/108 |
| 4,754,640 A * | 7/1988 | Fitzgerald | ............ | G01N 11/162 73/32 A |
| 4,811,593 A * | 3/1989 | Miura | ............ | G01N 11/162 73/54.26 |
| 4,920,787 A * | 5/1990 | Dual | ............ | G01N 11/162 73/54.41 |
| 5,048,323 A | 9/1991 | Stansfeld et al. | | |
| 5,517,850 A * | 5/1996 | Van Meter | ............ | G01N 11/14 411/305 |
| 5,596,139 A * | 1/1997 | Miura | ............ | G01F 23/2967 73/54.24 |
| 5,723,771 A * | 3/1998 | Miura | ............ | G01N 11/162 73/54.24 |
| 6,192,744 B1 * | 2/2001 | Henderson | ............ | G01N 11/165 73/54.24 |
| 7,392,842 B2 * | 7/2008 | Morgan | ............ | G01N 11/14 166/250.1 |
| 7,523,662 B2 * | 4/2009 | Drahm | ............ | G01D 11/10 73/290 V |
| 8,161,798 B2 * | 4/2012 | Jang | ............ | G01N 9/002 73/32 R |
| 8,266,949 B2 * | 9/2012 | Harris | ............ | G01N 11/10 73/54.28 |
| 9,116,092 B2 * | 8/2015 | Samaniuk | ............ | G01N 11/14 |
| 9,267,872 B2 * | 2/2016 | Haeusler | ............ | G01N 11/16 |
| 9,372,140 B2 * | 6/2016 | Sneujink | ............ | G01N 11/10 |
| 9,702,799 B2 * | 7/2017 | Gaugler | ............ | G01N 33/383 |
| 9,702,800 B2 * | 7/2017 | Morgan | ............ | G01N 11/14 |
| 9,719,904 B2 * | 8/2017 | Donzier | ............ | G01N 9/002 |
| 10,184,881 B2 * | 1/2019 | Goodbread | ............ | G01N 29/022 |
| 2005/0132782 A1 * | 6/2005 | Wallevik | ............ | B01F 7/063 73/54.28 |
| 2005/0262944 A1 * | 12/2005 | Bennett | ............ | B06B 1/06 73/592 |
| 2007/0186684 A1 | 8/2007 | Pham | | |
| 2008/0044705 A1 * | 2/2008 | Jang | ............ | G01N 9/002 429/414 |
| 2008/0105040 A1 * | 5/2008 | Bivens | ............ | G01N 11/14 73/54.28 |
| 2009/0120171 A1 * | 5/2009 | Harrison | ............ | G01N 11/16 73/64.53 |
| 2011/0061451 A1 * | 3/2011 | Harris | ............ | G01N 11/10 73/54.42 |
| 2013/0139576 A1 | 6/2013 | Goodbread et al. | | |
| 2013/0164620 A1 | 7/2013 | Haeusler et al. | | |
| 2013/0255371 A1 * | 10/2013 | Beaumont | ............ | G01F 1/05 73/196 |
| 2013/0340507 A1 * | 12/2013 | Brookfield | ............ | G01N 11/16 73/54.25 |
| 2014/0053638 A1 * | 2/2014 | Sneujink | ............ | G01N 11/10 73/54.28 |
| 2015/0075279 A1 * | 3/2015 | Donzier | ............ | G01N 9/002 73/32 A |
| 2016/0376398 A1 * | 12/2016 | Morley | ............ | C08G 59/502 523/400 |

FOREIGN PATENT DOCUMENTS

| | | | | |
|---|---|---|---|---|
| KR | 20120121422 A | * | 11/2012 | |
| RU | 2216007 C2 | * | 11/2003 | |
| WO | WO-2012033772 A3 | * | 6/2012 | ............ G01N 11/16 |
| WO | 2016166610 A1 | | 10/2016 | |

\* cited by examiner

Prior Art

TEMPERATURE COMPENSATED DENSITY VISCOSITY SENSOR HAVING A RESONANT SENSING ELEMENT

BACKGROUND

Field of the Invention

The field of the invention is fluid density measurement devices.

Background Art

Vibrational fluid density sensors are well known in the art. A typical vibrational density sensor consists of a resonator— either filled with or immersed in a fluid—that displaces said fluid as it vibrates. Due to inertial and viscous forces, the displaced fluid loads the resonator with additional mass (i.e. mass loading), increasing its inertia and decreasing its resonant frequency. In order to accurately determine the fluid's density, it is necessary to compensate for the effects of viscous forces, which entrain mass and contribute to the mass loading of the resonator.

The resonant frequency of a mechanical resonator depends on both its inertia and its elasticity. Consequently, other factors influencing either inertia or elasticity—such as mechanical stresses and temperature, other than variations in the density of the fluid—require compensatory adjustments to the measured resonant frequency.

Mechanical stresses may influence the resonant frequency of the resonator by eliciting changes in its vibrational response. This is true of, for instance, vibrating wires, whose vibrational frequency depends on their axial tension. Stresses in the wire's mounting means, whether through variable mounting forces or thermal expansion, may cause its resonant frequency to vary unpredictably, decreasing the accuracy of the measurement.

In general, the elastic behavior of resonators is influenced by their temperature. If the temperature of the resonator is known, and in the absence of hysteresis effects (a lack of deterministic relationship between temperature and elastic properties), it is possible to correct for the influence of temperature on the resonator's frequency. Resonators that are completely immersed in the fluid whose density they are meant to measure can attain uniform temperature, enabling accurate correction of thermal influences on resonant frequency. Similarly, resonators that are completely filled with the fluid, and which have low heat capacity and are surrounded by thermal insulation, may attain uniform temperature. Under such conditions, the frequency of the resonator under unloaded conditions may be calculated and used to calculate the fluid's density. However, resonators that are only partially immersed in a fluid may have non-uniform temperature distributions, making calculation of their unloaded frequency difficult, and imposing limitations on the potential accuracy of the density measurement.

U.S. Pat. No. 9,267,872 discloses a symmetric coaxial resonator that is capable of measuring the product of the density and viscosity of a fluid in which it is immersed. The sensor exposes a cylindrical surface to the fluid, which surface oscillates in torsion, and is therefore affected by shear stresses caused by shearing the fluid in contact with said surface. It is known that such torsionally oscillating sensors experience an increase in their damping due to viscous dissipation in the fluid in which they are immersed. Said viscous dissipation is, at least for a Newtonian fluid, dependent on the product of density and viscosity of said fluid. Said torsionally oscillating sensor also experiences a decrease in its resonant frequency, which frequency decrease is due to an increase of rotational moment of inertia caused by fluid dragged along by said shearing motion of said fluid. Said increase in said moment of inertia cannot easily be separated from the effects of viscosity, since said additional mass of fluid dragged along by the shearing of said fluid is equally dependent on the density and the viscosity of said fluid.

If said oscillating body is flattened rather than cylindrical, so that at least a portion of said body moves perpendicularly to its own surface, said perpendicular motion displaces fluid, increasing the mass loading of said body and decreasing its resonant frequency by an amount greater than that caused by viscous entrainment of additional mass. By measuring both the frequency decrease and the damping of such a flattened torsionally oscillating body, it is possible to measure both the density and the product of density and viscosity, and therefore to derive a value for viscosity from said measured values.

It is known that such oscillating bodies have a resonant frequency that is influenced by both the rotational inertia and the torsional elasticity of such a body. More particularly, when the body is constructed as a lumped-constant resonator, then the inertia is predominantly determined by torsional masses, and the elasticity by torsional springs. It is known that for most materials from which springs may be made, the elastic properties of the spring are dependent on the temperature of the spring. Therefore, the temperature of the spring in such a system must be known, as well as the relationship between the temperature of said spring and its elastic properties. The accuracy of a density sensor constructed with such a mass-spring system is therefore dependent on the accuracy with which the frequency of said sensor when not loaded by fluid can be predicted from its temperature.

Determining the temperature of the spring is only directly possible when said spring is isothermal, that is, when all of its parts are at the same temperature. This is achieved in resonators that are completely immersed in fluid, as in patent application US 20130139576, which discloses coupled torsional resonators completely immersed in a fluid.

Prior art solutions to the problem of simultaneously measuring density and viscosity of a fluid using a completely immersed resonator are limited in part by their use of magnetic and piezoelectric transducers. In the case of magnetic transducers used to excite and/or sense the sensor's resonant characteristics, the presence of magnetic particles may severely compromise the sensor's performance when the transducers are so configured that magnetic particles in the fluid may accumulate on or near the sensor's active element. Similarly, when the transducers include soft magnetic elements that are biased by external fields, it is still necessary to have bias, excitation and sensing coils in close proximity to the active element, which complicates the construction of the sensor in addition to creating narrow passages in which bits of debris may become lodged, compromising the sensor's resonant behavior. Piezoelectric transducers that are immersed in the fluid under test are subject to breakage, as well as corrosion of their electrodes. In addition, electrical feedthroughs are necessary to conduct signals to and from the transducers. Such feedthroughs are susceptible to leaks and corrosion effects, especially when the transducer is operated under conditions of high temperature and pressure, and/or in the presence of corrosive fluids. Additionally, piezoelectric transducers that operate indirectly on a resonator, as through a compliant pressure barrier, are subject to errors due to unpredictable thermal and mechanical behavior of the compliant pressure barrier under the influence of hydrostatic pressure and temperature gradients.

Devices to measure fluid density in a laboratory environment are well known. Generally, a suitably mounted elastic U-shaped tube equipped with suitable transducer means to excite and measure its motion, is filled with the fluid under test, and the shift in its resonant frequency is measured. The difference in frequency between when the tube is empty and when it is filled with the fluid can be used to calculate the fluid's density. However, this known device is not well suited to measuring density in a process environment, since a portion of the process fluid must be diverted through its vibrating tube, which is typically of much smaller diameter than the process line.

Measuring fluid properties downhole in oil, gas, and geothermal drilling and production poses other challenges that prohibit the use of known commercial sensors. Although the vibrating U-tube sensor can measure density at high pressure and temperature, it is not suitable for downhole use in oil and gas exploration and production. It is also limited to measurement of density alone, so a second, independent instrument must be used to measure viscosity. Vibrating wires, tubes, and tuning forks are known as resonant measurement elements for downhole use, but they are expensive, fragile, and unavailable for commercial applications.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

A method of measuring density of a target fluid, that utilizes a fluid density measurement device, which includes a housing, defining a chamber and an aperture; a resonator having length that is at least 5 times greater than its smallest diameter and having a longitudinal axis and nodal plane, transverse to the longitudinal axis, and that includes a tube having a first end and a second end and being closed at the second end by a second-end closure, and being attached to the housing at the nodal plane, which is sealingly joined to the aperture, blocking fluid ingress, and so that an enclosed resonator portion extends into the chamber and an exposed resonator portion extends outside of the chamber; and further including a drive rod centrally attached to the second-end closure and extending into the enclosed resonator portion; and a transducer assembly. The method begins with the placement of the exposed portion of the resonator in the target fluid and placing and maintaining the resonator into an isothermal state, the transducer assembly is used to excite the resonator so that the exposed portion vibrates perpendicularly to a portion of its own surface and to sense resultant resonator vibrations. Finally, the resultant vibrations are analyzed to determine density of the target fluid.

A fluid density measurement device that includes a housing, defining a chamber and an aperture; a resonator having length that is at least 5 times greater than its smallest diameter and having a longitudinal axis and a nodal plane, transverse to the longitudinal axis. The resonator further includes a tube having a first end and a second end; a second-end closure, closing the second end; and a drive rod centrally attached to the second-end closure and extending to the tube first end. Further, the device includes a resonator transducer assembly and the resonator is sealingly joined to the aperture at the nodal plane, blocking fluid ingress, and so that an enclosed resonator portion extends into the chamber and an exposed resonator portion extends outside of the chamber, and wherein the chamber tends to assume the temperature of the exposed resonator portion. This causes the resonator to be isothermal, and wherein the resonator transducer assembly drives the resonator such that the exposed portion vibrates perpendicularly to a portion of its own surface.

A method of measuring density of a target fluid that utilizes a fluid density measurement device, which includes a housing, defining a chamber and an aperture; a resonator having length that is at least 5 times greater than its smallest diameter and having a longitudinal axis and nodal plane, transverse to the longitudinal axis, and that includes a tube having a first end and a second end and being closed at the second end by a second-end closure, and being attached to the housing at the nodal plane, which is sealingly joined to the aperture, blocking fluid ingress, and so that an enclosed resonator portion extends into the chamber and an exposed resonator portion extends outside of the chamber; and further including a drive rod centrally attached to the second-end wall and extending into the enclosed resonator portion. The device further includes a resonator transducer assembly; and a first temperature measurement device in the enclosed portion and a second temperature measurement device in the exposed portion. The method includes placing the exposed portion of the resonator in the target fluid, using the transducer assembly to excite the resonator so that the exposed resonator portion vibrates perpendicularly to a portion of its own surface; and analyzing the resultant vibrations and the measurements of the first temperature sensor and the second temperature sensor to determine density of the target fluid.

The present application describes, in one embodiment, a combined density-viscosity sensor suitable for process, downhole and laboratory use that is accurate, robust, and economical to build and operate.

This application, in one embodiment, discloses a density-viscosity sensing method that solves the problems of conventional density and viscosity sensing means. The present application describes methods for making sensors that solve the foregoing problems by reducing or eliminating the problem of thermal non-equilibrium on a density and viscosity measuring resonator.

In addition to the exemplary aspects and embodiments described above, further aspects and embodiments will become apparent by reference to the drawings and by study of the following detailed descriptions.

BRIEF DESCRIPTION OF DRAWINGS

Exemplary embodiments are illustrated in referenced drawings. It is intended that the embodiments and figures disclosed herein are to be considered illustrative rather than restrictive.

PREFERRED MODES OF CARRYING OUT THE INVENTION

When used in this application with respect to a resonator as disclosed below, the term "isothermal" means that the average temperature of the enclosed resonator portion is not more than 5° C. different from the average temperature of the exposed resonator portion.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

In a preferred method, which may be used either alone or in combination with one of the presently described methods, the temperature of a substantially isothermal resonator is measured, followed by determination of any departures from the isothermal condition of the resonator, which are determined by one or more temperature measurements taken at various locations on said resonator. These temperature measurements are used to correct for the assumption of the resonator's isothermal condition, and thus correct the measured values of resonant frequency and damping for changes in characteristics of said resonator, as determined by the temperature of said resonator. Signal processing and evaluation means are then employed to measure at least the resonant frequency and damping of the resonator, and algorithmic calculation means are further used to derive values of fluid properties from said resonant frequency and damping.

Figure 1:
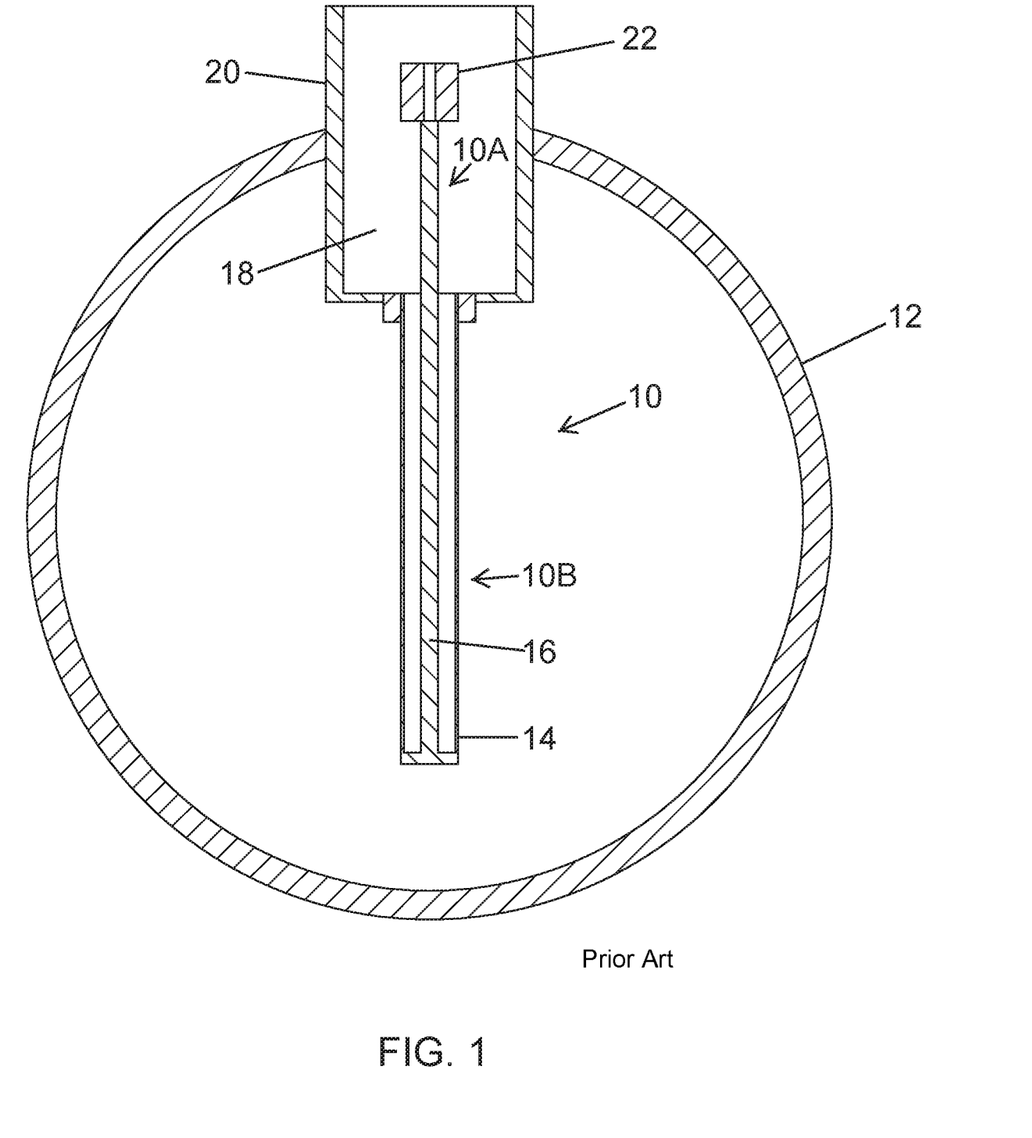
FIG. 1 shows a sectional view of a prior art co-axial resonator mounted within a pipe.

Referring to FIG. 1, in a prior art device, a density viscosity sensor possesses isothermal resonator 10 that is sensitive to temperature changes in the fluid in which it is immersed. Co-axial resonator 10 is mounted within a pipe 12, with at least one end of resonator 10 immersed in a fluid whose properties are to be determined, wherein said properties include but are not limited to density and viscosity. The resonator 10 vibrates transversely, so that its surface moves perpendicularly to itself, displacing fluid, displaced fluid places an inertial load on the resonator 10, making it sensitive to the density of the fluid. The resonator 10 consists of an outer tube 14 and a drive rod 16 (which may be hollow, thereby being in the form of a tube) placed inside the outer tube 14, and attached at the outer tube's free end that is immersed in fluid. The free end of the inner rod or tube 16 extends backward toward the fixed end of the outer tube 14 into a chamber 18 defined by a housing 20. Resonator 10 is connected at its nodal point to housing 20, such that one portion of said resonator 10 is an enclosed portion 10A and another portion, is an exposed portion 10B, which is immersed in fluid to take a fluid properties measurement. Housing 20 consists of material impervious to fluid ingress. Since making an accurate density measurement requires knowing the resonant frequency of the resonator when it is not loaded by a fluid, and since the resonator's resonant frequency is dependent on its temperature, the non-uniform temperature of resonator 10 in FIG. 1 makes it impossible to accurately know the resonator's unloaded frequency, and therefore prohibits making an accurate density measurement.

A goal of the invention is to ensure that resonator 10 remains substantially isothermal, such that both the housing 20 and the end of the resonator 10 immersed in the fluid attain a similar temperature to that of the fluid, despite the exposure of housing 20 to a different ambient temperature outside of pipe 12.

Figure 2:
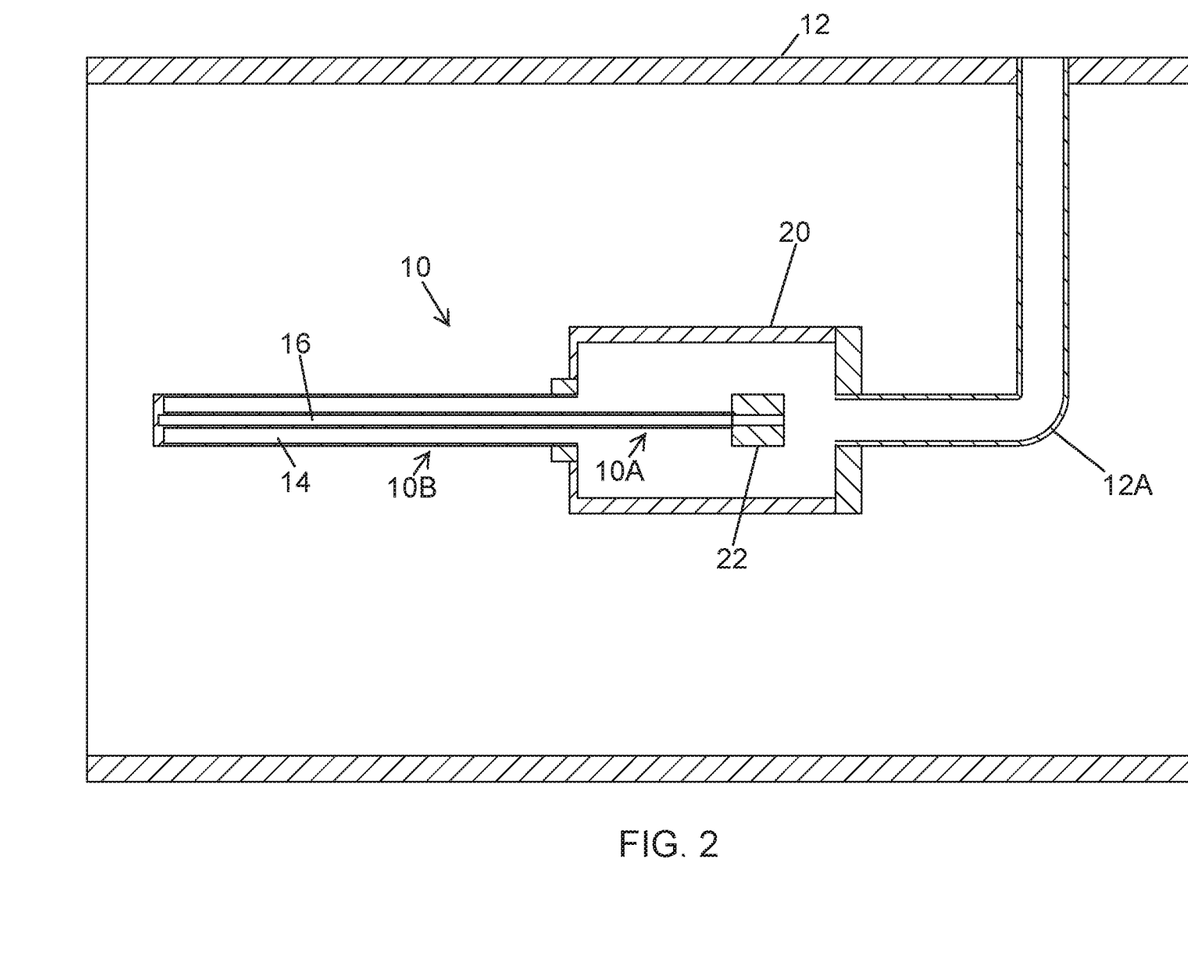
FIG. 2 is a sectional view of a transversely vibrating resonator mounted on one end of a bent pipe.

Referring to FIG. 2, which shows a first preferred embodiment, a housing 20, supporting a transversely vibrating resonator 10 is mounted on one end of a bent pipe 12A. Bent pipe 12A is preferentially made of a thermally insulating material; consequently, in holding the sensor completely immersed in the fluid, the pipe 12 ensures that both the exposed part of the resonator 10 and the housing 20 of the sensor reach equilibrium with the temperature of the fluid. The resonator 10 is essentially isothermal, with enclosed portion 10A approximating the temperature of the exposed portion 10B, so that its unloaded resonant frequency can be determined as long as the temperature of the fluid is known. The support pipe 12A is also used as a conduit for electrical connections to the transducer element 22 affixed to the free end of the inner rod 16 of the resonator 10. The entire transducer also includes an additional element (not shown) that exerts a force upon element 22, exciting the resonator 10 in a bending mode, and also sensing the resonator's transverse motion. In a preferred embodiment transducer element 22 is a permanent magnet, which is driven by an electromagnet assembly (not shown) mounted in housing 20. Because the outer tube 14 vibrates perpendicularly to its own surface, fluid is displaced, causing its vibratory inertia to increase by an amount dependent on the fluid's density, resulting in a decrease in the sensor's resonant frequency compared to its resonant frequency in the absence of a surrounding medium (e.g. in vacuum).

Figure 3:
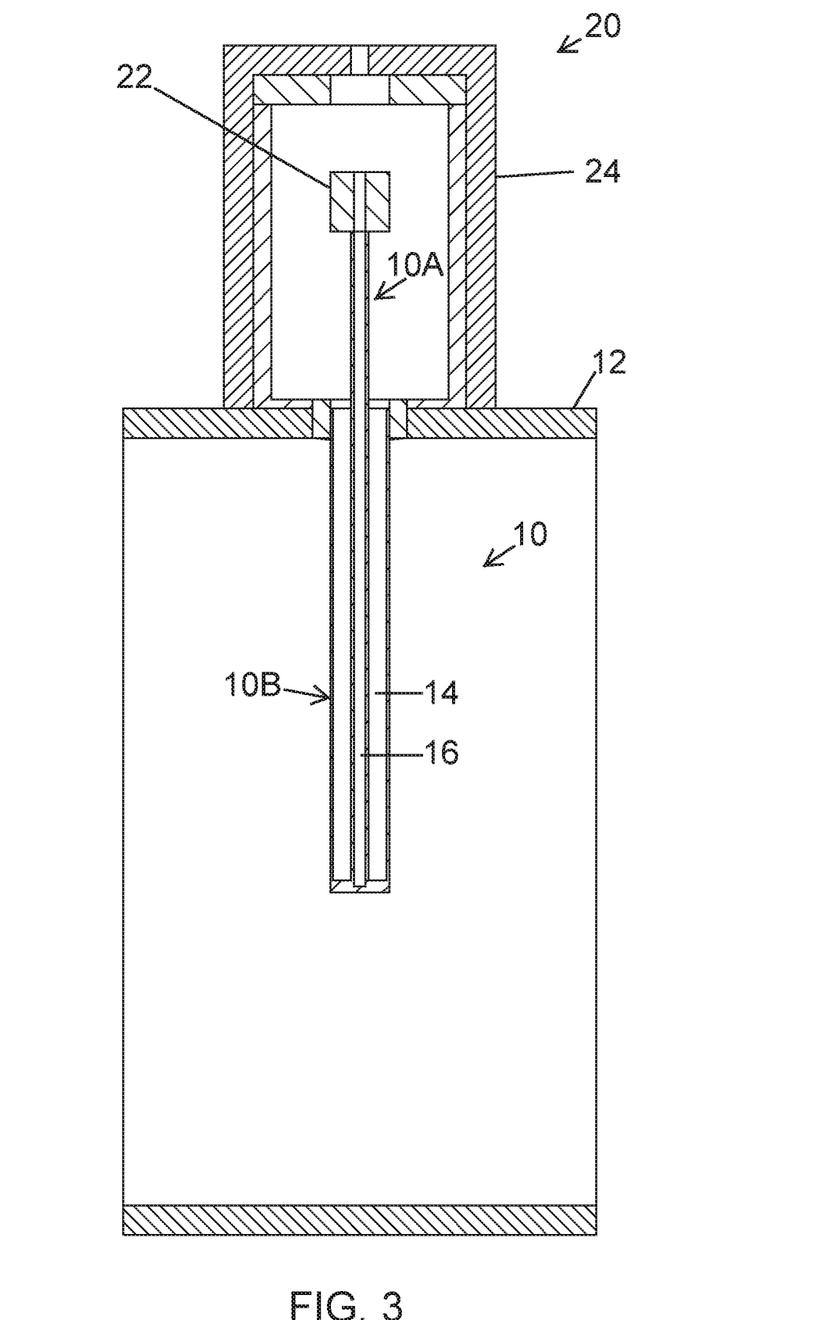
FIG. 3 is a sectional view of a transversely vibrating sensor mounted radially in a pipe.

Alternatively, transversely vibrating sensor may be mounted radially within a pipe 12, as shown in FIG. 3, which illustrates a second preferred method. Those parts of the body of the sensor not in immediate contact with the fluid are covered by a high-efficiency insulating sheath 24, which renders the covered parts of the sensor essentially adiabatic. Since heat is neither lost nor gained by the enclosed part 10A of the resonator 10, all of its parts eventually come into equilibrium with the exposed portion 10B, making the resonator 10 isothermal with a temperature equal to that of the fluid.

Figure 4:
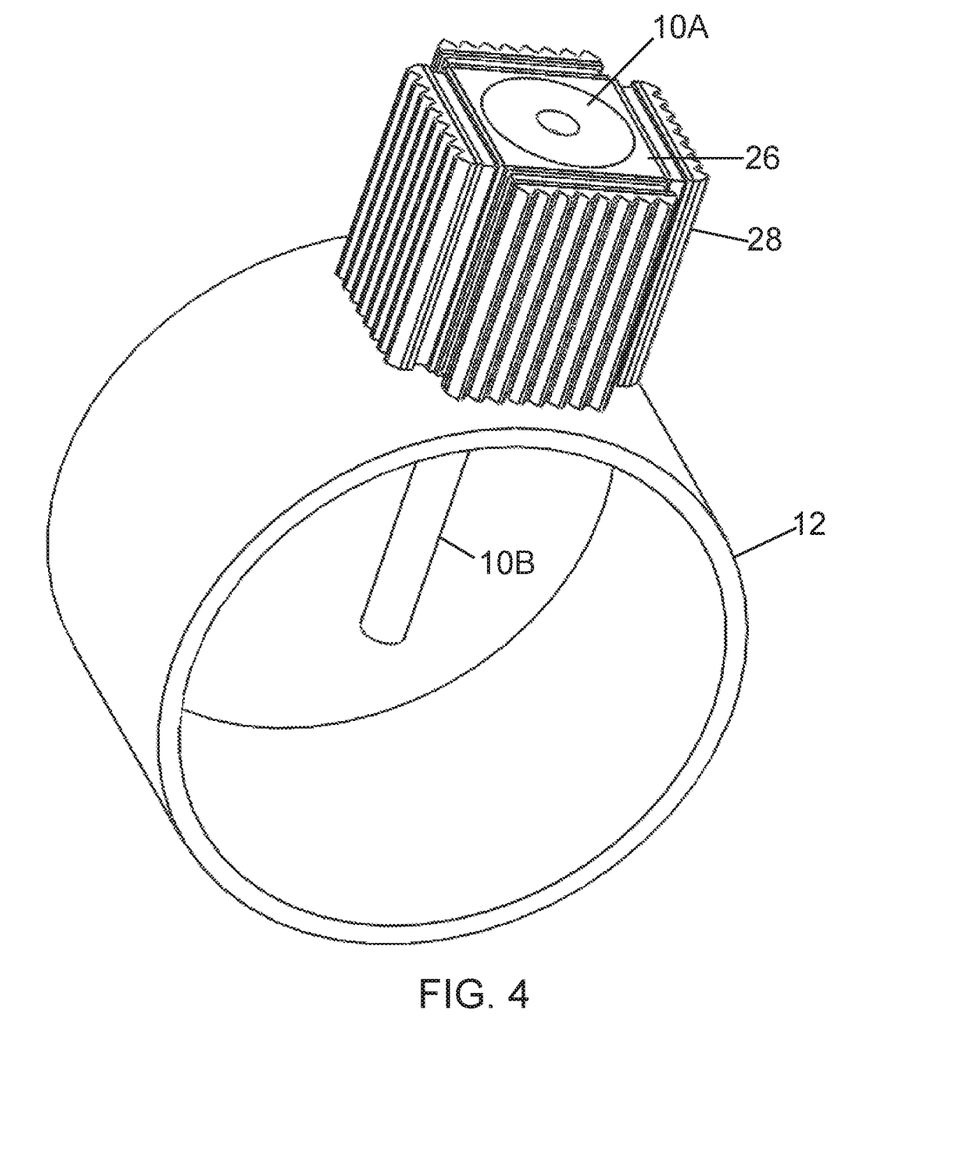
FIG. 4 is an isometric view of the transversely vibrating sensor of FIG. 3 surrounded by a thermally conductive block and Peltier devices, respectively.
Figure 5:
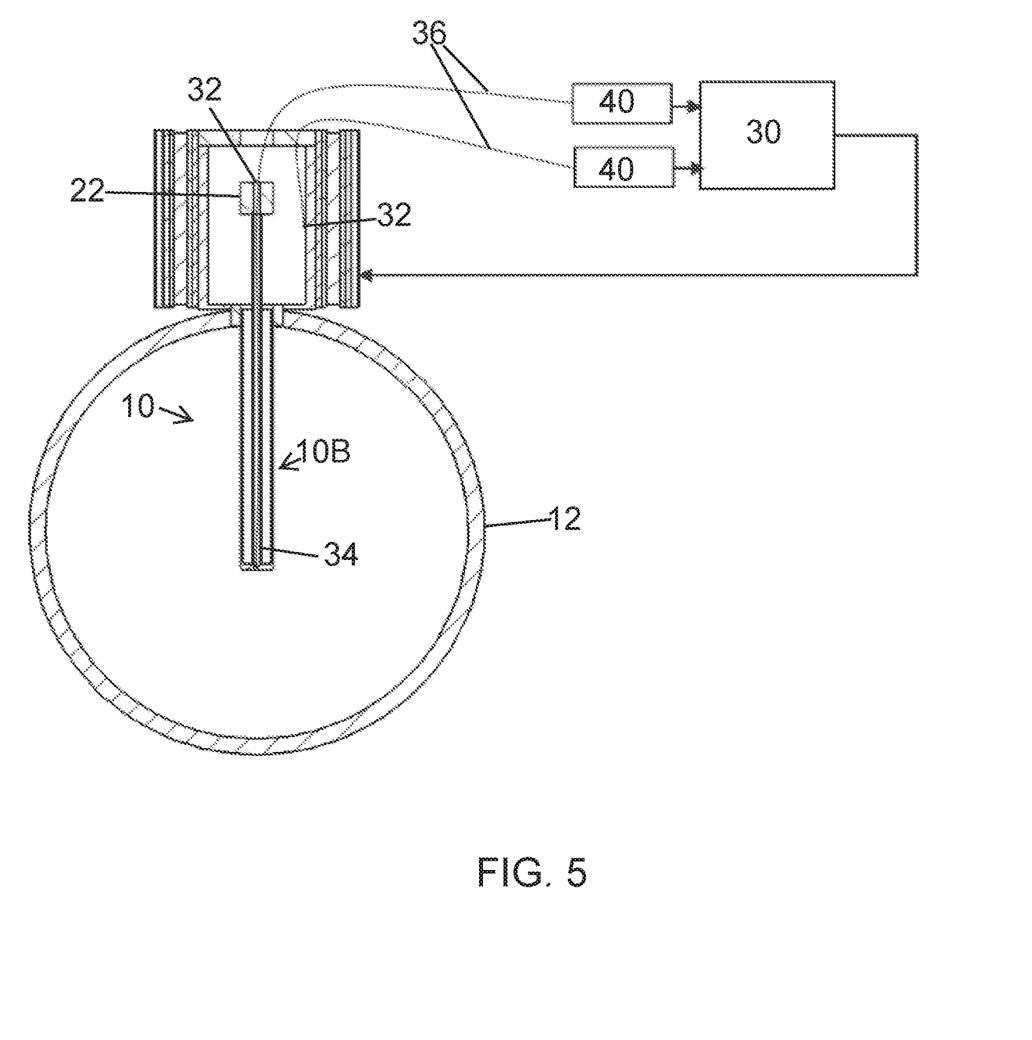
FIG. 5 is a sectional view of the transversely vibrating sensor of FIG. 4, showing the paths to the thermocouples and controller.

In a third preferred method, shown in FIGS. 4 and 5, which may be used either alone or in combination with one of the presently described methods, the non-immersed portion of resonator housing 20 (Shown in FIGS. 1-3) possesses means for heating and/or cooling said portion of said housing. The enclosed portion of sensor 10A is surrounded by a thermally conductive block 26, in turn surrounded by an array of Peltier devices 28, which are connected to appropriate power supply and control means 30 capable of maintaining said sensor body at a preset temperature (as shown in FIG. 5). These temperature regulation means accept a temperature measurement from a model or a temperature sensor located in the exposed portion 10B of resonator 10, and calibrates/adjusts the temperature of said non-immersed portion of resonator housing 20 to the temperature of said immersed portion of said resonator 10. Said two temperatures are compared, and their difference is used as the error signal for a controller 30 that adjusts the power input to the Peltier heater/cooler 28 so as to drive said temperature difference to zero. These temperature regulation means together with said heating and/or cooling means constitute a system for maintaining the resonator 10 in an isothermal condition. This process causes the resonator 10 to become essentially isothermal. In alternative embodiments, other types of heating and cooling devices, other than Peltier devices 28, are used.

The accuracy of the first preferred method is based on the assumption that the insulation of the non-immersed end of the sensor is sufficient to ensure that the resonant element is isothermal. Similarly, the accuracy of the second preferred method is based on the assumption that the thermal conductivity of the housing 20 protecting the non-immersed portion of the sensor is sufficiently high, and that its heat transfer to surrounding structures is sufficiently low, that its temperature is substantially the same as that of the immersed end of the resonator 10. Similarly, the accuracy of the third preferred method depends on the efficacy of the Peltier heating/cooling system 28 to maintain the body at the same temperature as the fluid end of the resonator 10.

Figure 6:
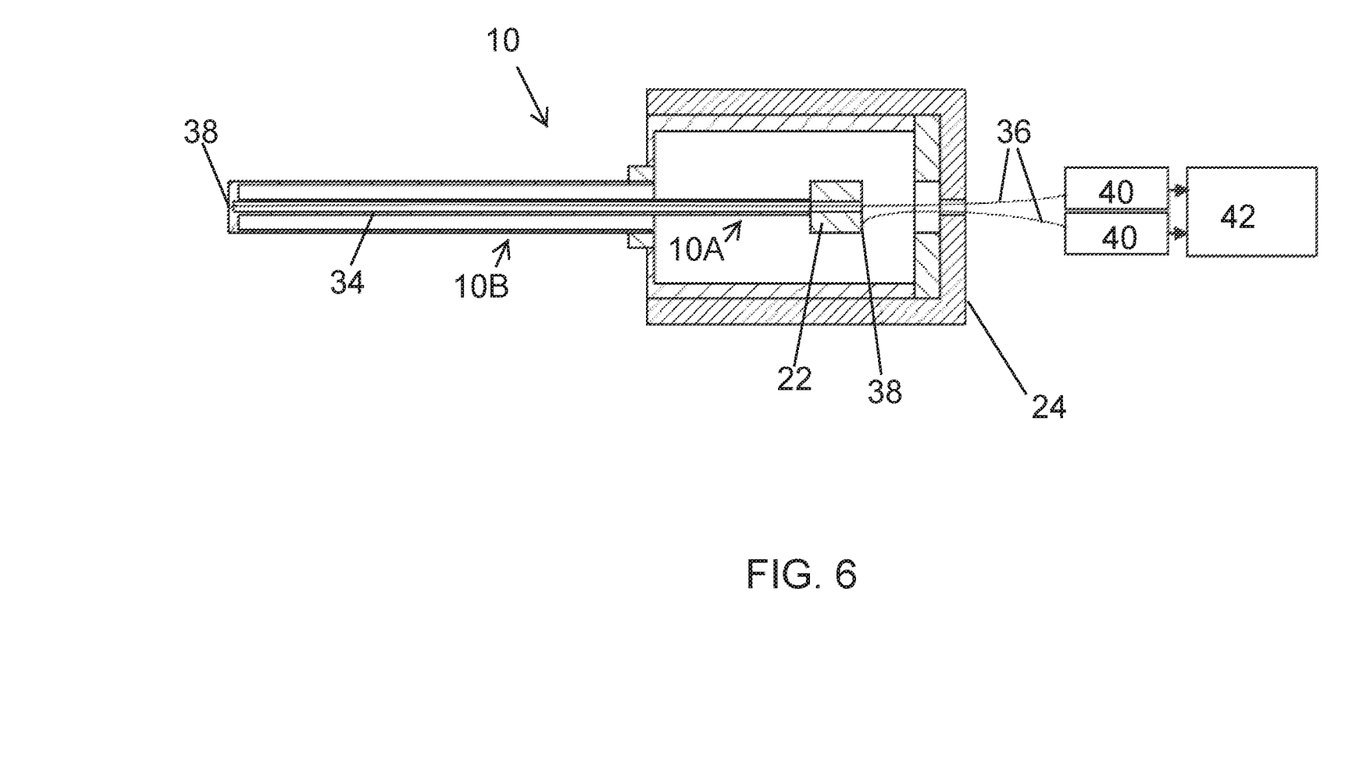
FIG. 6 is a more detailed sectional view of the sensor of FIG. 3, showing the disparate locations of two thermocouples.

A fourth preferred method, illustrated in FIG. 6, which may be used either alone or in combination with one of the presently described methods, consists of providing means to measure the temperatures of at least two locations within resonator 10, and providing a model to predict the unloaded resonant frequency of said resonator 10 based on the measured temperatures of at least two locations within resonator 10. In one variant, based on the first preferred method, housing 20 preferentially includes thermally insulating material 24, and at least two temperature sensors 32 (FIG. 5) are placed at at least two locations on the sensor, typically at the tip and the transducer end 22. In a preferred embodiment, the inner rod is replaced by a hollow tube 34, to permit conducting the leads for the temperature sensor to the free end of the resonator 10. The transducer 22 is also provided with a through hole to permit the exit of the temperature sensor leads 36. Similarly, a second temperature sensor 32 is attached to the transducer end 22 of the resonator 10. The temperatures measured from at least two locations within resonator 10 are used in a predictive model to correct for imperfections in the measures used to make the sensor's resonator isothermal. In a preferred embodiment, the temperature sensors are thermocouples 38, as these can be fabricated from very fine wire whose mass and rigidity are negligible compared to the resonator's 10, and thus have negligible influence on either the resonator's frequency or damping. The two thermocouples' 38 outputs are amplified by the thermocouple amplifiers (TC amp) 40 and serve as inputs to an algorithm stored in the processor 42 which predicts the unloaded frequency of the resonator (FIGS. 5 and 6). Further, the predictive model and the measured temperatures of at least two locations within resonator 10 are used by an algorithm to predict the density and viscosity of the fluid given the damping, resonant frequency, and unloaded resonant frequency of said resonator 10. The better the initial isothermal condition of the resonator 10, the more accurate the compensation by this method. This computational method for correcting residual departures from isothermal conditions may equally well be applied to the second or third preferred methods described above to improve its accuracy.

It is further understood that the two-point temperature measurement is merely illustrative of a more general compensation method. In cases where a two-point measurement does not provide sufficient accuracy, it is possible to use three or more measurements together with suitable models for temperature distribution in the resonant sensor. Additionally, it is further understood that, although the sensors in the foregoing embodiments were shown with generic transducers, said transducer means may be selected from the group of piezoelectric, capacitive, electromagnetic, magnetostrictive, optical, or any other transduce means capable of exciting the desired resonance in the resonator, and/or of measuring the resonant response of said resonator.

The foregoing embodiments make use of a coaxial bending resonator. However, any resonator may be used provided it vibrates perpendicular to its own surface over at least part of its surface. In the following descriptions of preferred embodiments, it is to be understood that these all can be rendered nominally isothermal using the techniques of immersion and/or insulation described above, and that the accuracy of the immersed and/or insulated sensor can be enhanced by means of the temperature measurement and compensation scheme described in the foregoing section.

Bending resonators that vibrate transversely, such as the one described above, have the disadvantage of being vibrationally unbalanced. As the tubular section vibrates, it exerts substantial reaction forces on the resonator's body, which may give rise to energy leakage into the supporting structures—which, in turn, introduces uncertainty into both the unloaded resonant frequency and the unloaded damping of the resonator. In another preferred embodiment, the density viscosity sensor consists of a balanced resonator, in which two coupled resonant elements are joined together in such a way that the reaction forces on their common mounting are largely neutralized, resulting in superior isolation from mounting influences compared to an unbalanced resonator. A common tuning fork is an example of a balanced bending resonator. Prior art teaches the use of both bending and torsional immersed tuning forks to measure fluid properties. These have the disadvantage, however, of being difficult to drive and sense without also immersing the transducer(s) in the fluid being measured.

Figure 7:
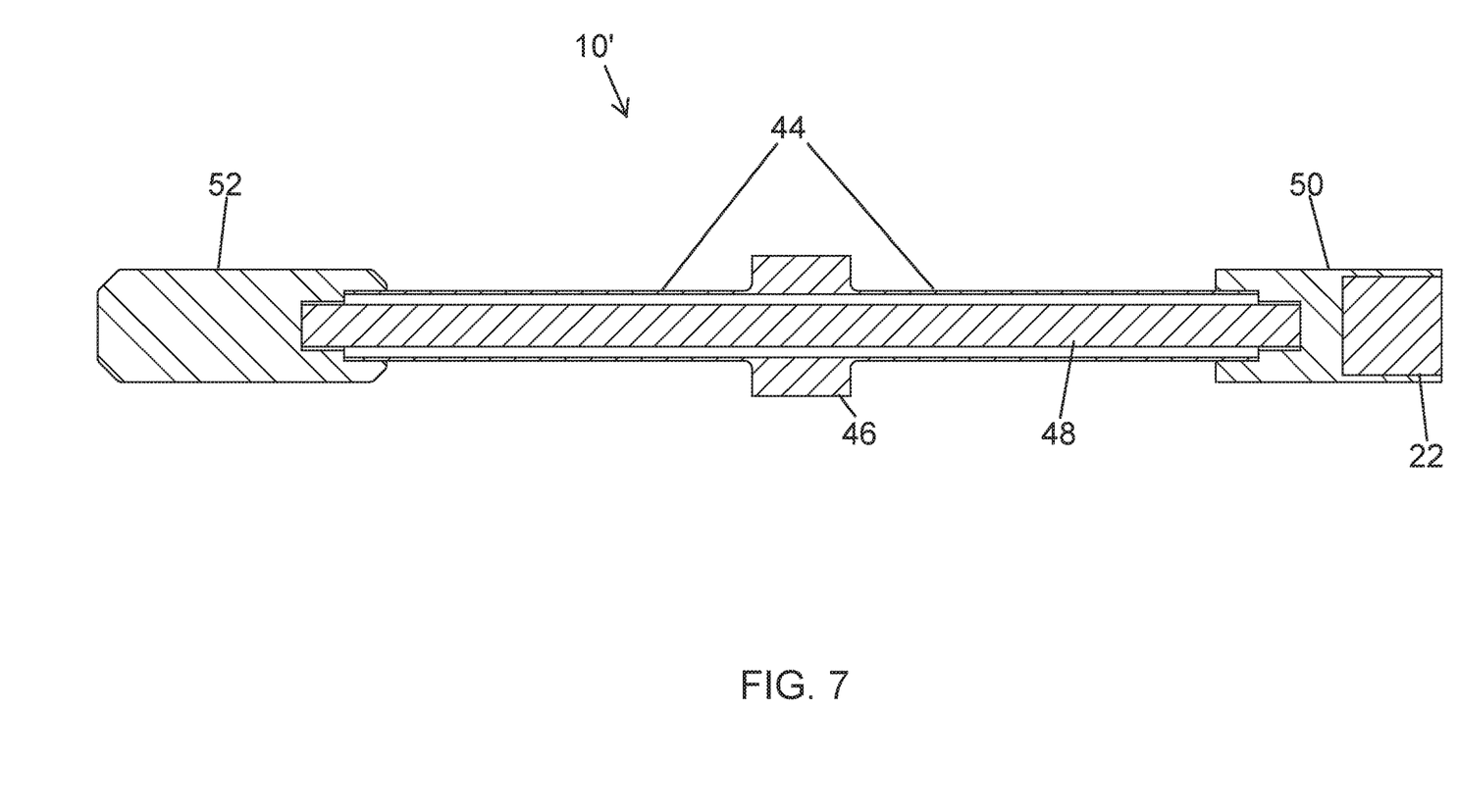
FIG. 7 shows a sectional view of a symmetrical resonator having a fluid end mass and a transducer end mass mounted on a coupling rod.

Another kind of balanced resonator that does not have these disadvantages is disclosed in U.S. Pat. No. 9,267,872. Referring to FIG. 7, balanced resonator 10' consists of a torsion spring in form of a tube 44 symmetrically configured about a nodal hub 46. Coupling rod 48 joins the transducer end mass 50, driven in torsion by transducer means not further described here, and the fluid end mass 52. The fluid end mass 52 is dimensioned so as to have the same moment of inertia as the transducer end mass 50, so that the entire assembly vibrates as a symmetrical resonator, the desired mode being that in which the two ends twist in opposite directions. When vibrating in this mode, there is no net torque exerted on the nodal hub 46.

Figure 8:
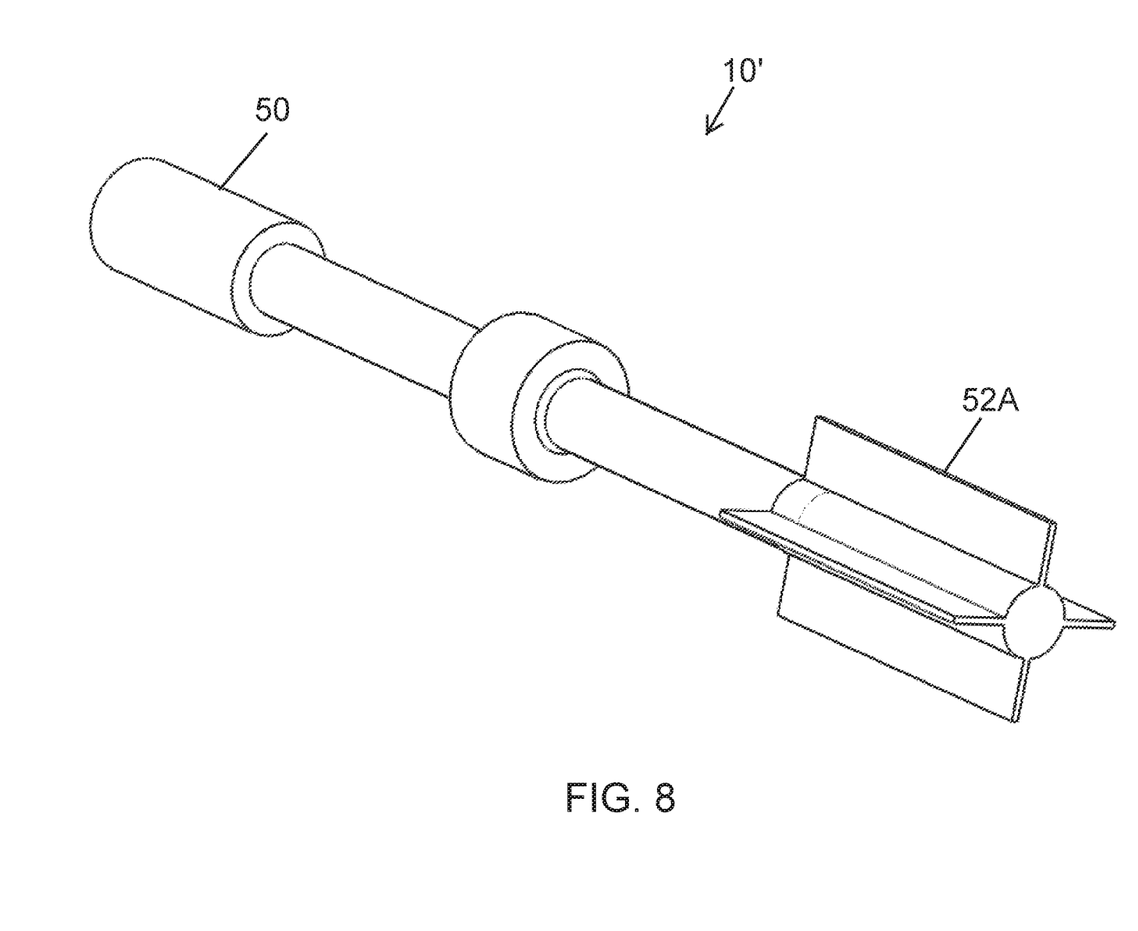
FIG. 8 depicts a symmetric resonator with a flattened fluid end mass having four radial fins.

The resonator disclosed in U.S. Pat. No. 9,267,872 possesses a cylindrical fluid end mass 52, making it sensitive to the product of viscosity and density. In order to separate the effects of density and viscosity in a torsional resonator 10', it is necessary to flatten at least part of the fluid end mass 52 so that, when vibrating in torsion, it moves perpendicularly to its own surface. A preferred embodiment of such a flattened fluid end mass is as shown in FIG. 8, which possesses a series of radially disposed fins. The flattened parts 52A of the fluid end mass 52A have a component of velocity perpendicular to their own surface when vibrating in torsion about its the longitudinal axis. Fluid end mass 52A displaces fluid as it vibrates, increasing the mass loading and increasing its moment of inertia. This increase of moment of inertia lowers the resonant frequency of the resonator 10', making it sensitive to fluid density. At the same time, portions of the resonator 10' move parallel to their own surfaces, producing shearing motion in the fluid and loading the resonator with viscous forces. These viscous forces dissipate energy, increasing the damping of the resonator 10'. Therefore, the increase of damping and reduction of frequency when the flattened end of the resonator 10' is immersed in a fluid can be used to calculate the density and viscosity of the fluid.

In order to measure fluid density with this symmetric torsional resonator 10', it is necessary to know its resonant frequency when it is not loaded by fluid. This unloaded resonant frequency is, as is the case with all resonators disclosed in this application, dependent on the temperature of the resonator. And as in the other resonators, unless the resonator is isothermal, it is difficult or impossible to predict its unloaded resonant frequency with good accuracy.

Figure 9:
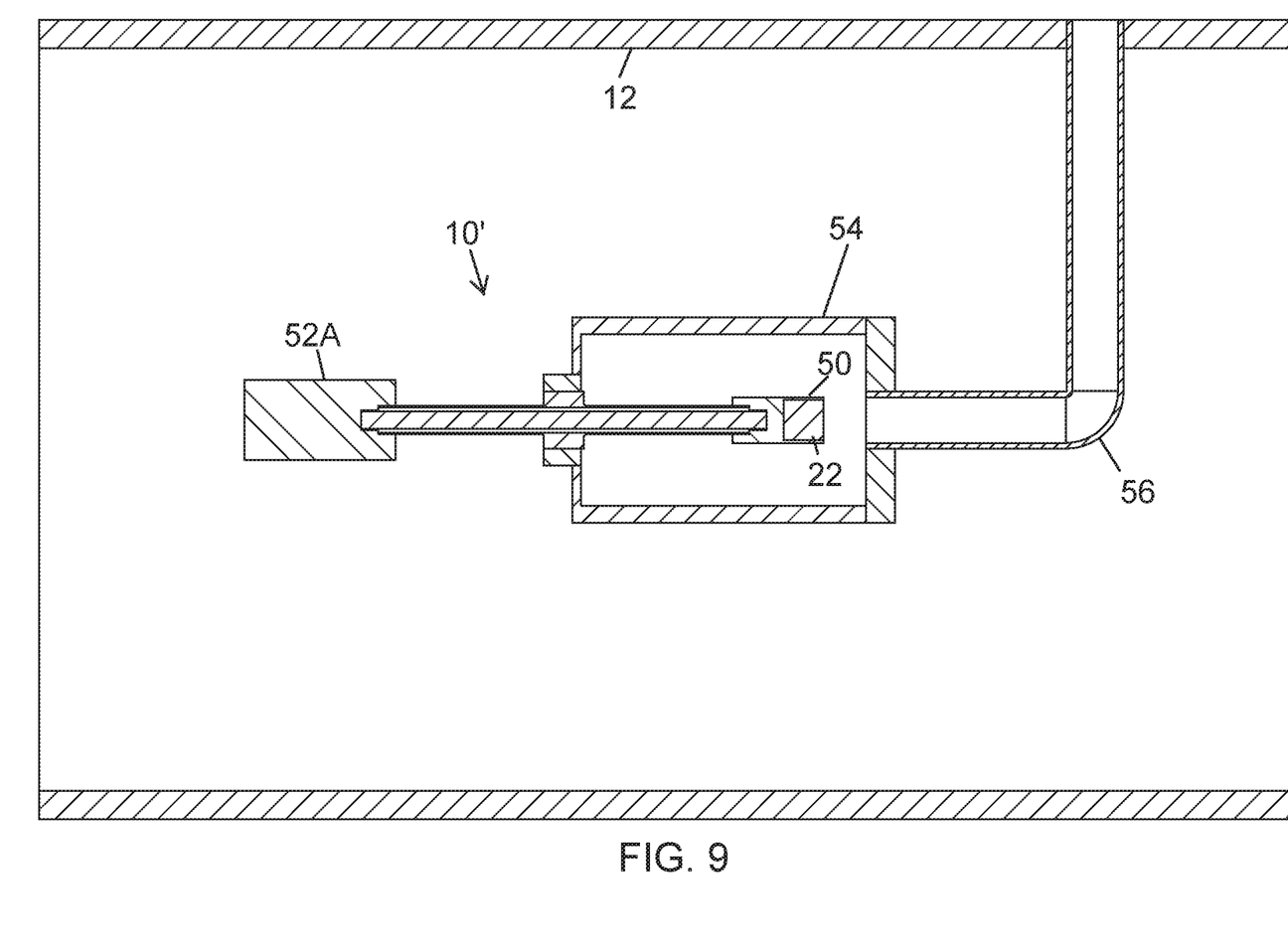
FIG. 9 is a sectional view of a symmetric resonator with its transducer end enclosed in a thermally conductive body, attached to the wall of a pipe by a thermally-insulating support, and having a flattened fluid end mass.

FIG. 9 shows a symmetric torsional resonator 10' with its transducer end enclosed in a thermally conductive body 54, attached to the wall of a pipe 12 by a thermally insulating support 56. This renders the entire resonator essentially isothermal, although it is understood that in cases where there is a minor temperature difference between the fluid end mass 52A and the transducer end mass 50, an additional temperature compensation step may be implemented in the methods described above, where temperature sensors are used to measure the actual temperatures at both ends of the resonator and this information used to calculate a correction factor for the unloaded resonant frequency of the resonator.

This configuration is particularly favorable for use in devices to measure the viscosity and density of fluids downhole in oil and gas drilling, wireline logging and production logging operation since the environment downhole is typically isothermal.

Figure 10:
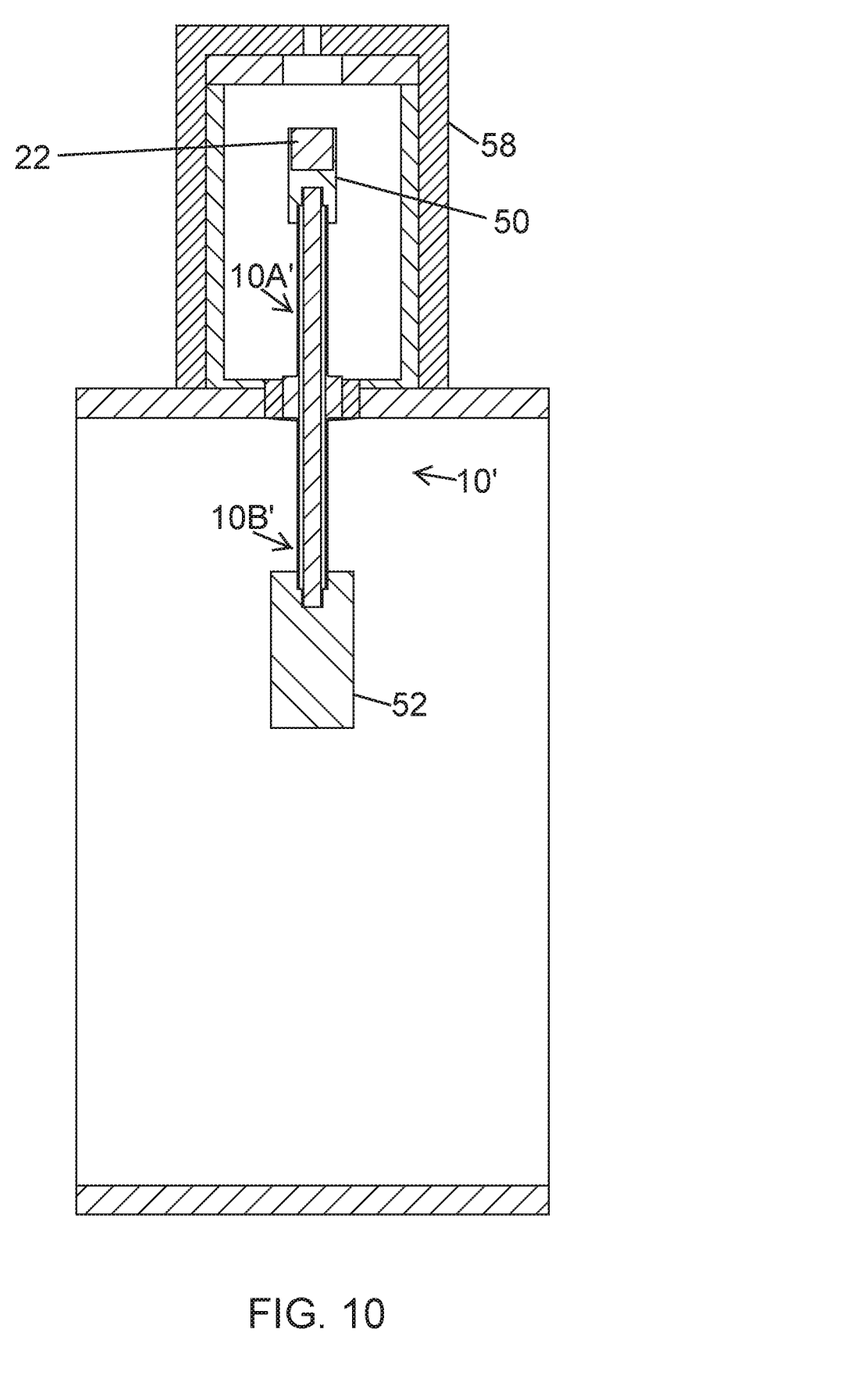
FIG. 10 is a sectional view of a symmetric torsional resonator with a flattened fluid end mass, with a thermally insulating sheath surrounding its transducer end mass.

Referring now to FIG. 10, a preferred embodiment of a fluid properties (including density) measurement device 10, includes a symmetric torsional resonator 10' that is shown with a flattened end 52. Also, a thermally insulating sheath 58, surrounding a housing 54 (FIG. 9), which defines a chamber 18 (FIG. 1). As in FIG. 3, the sheath prevents thermal exchange with the ambient environment, keeping the symmetric resonator 10' essentially isothermal with the fluid temperature. This embodiment may further include the temperature measurement elements shown in FIG. 6, so that, minor temperature differences between the enclosed portion 10A' and the exposed portion 10B' may be measured, and the temperature difference used to algorithmically compensate for the temperature difference. It is further understood that the insulating sheath may be replaced by the heating/cooling system as shown in FIGS. 4 and 5 with substantially the same function when applied to the system of FIG. 10.

Figure 11:
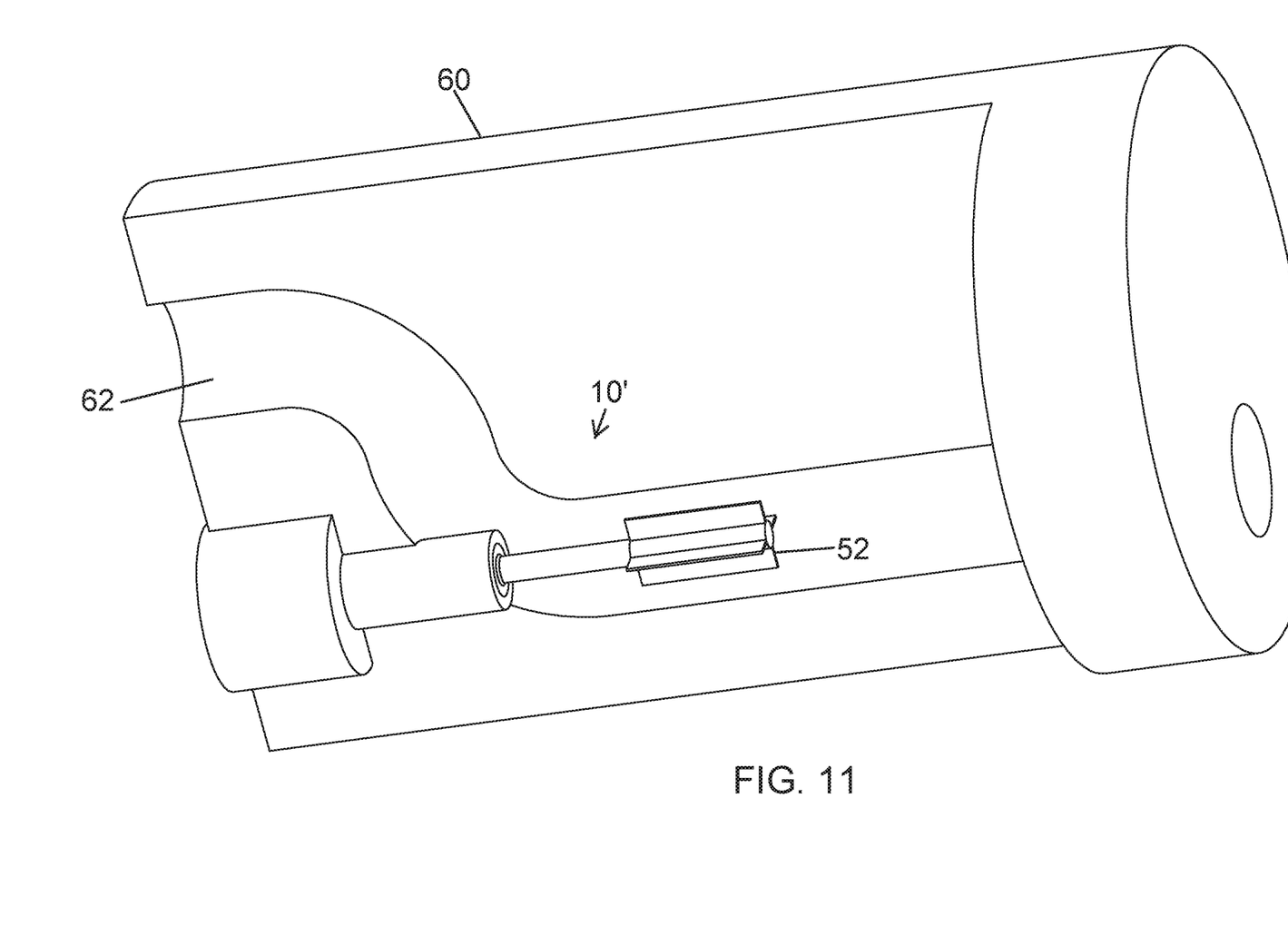
FIG. 11 is a cut-away view of a symmetrical density-viscosity sensor mounted in a section of a wireline tool.

In another embodiment as shown in FIG. 11, an illustrative embodiment of a symmetrical density-viscosity sensor 10' is mounted in a section of a wireline tool 60 of the type that is placed in boreholes to evaluate rock formations and formation fluids. The sensor may also be mounted perpendicularly to the tool axis within part of the flow channel 62 to facilitate easier mounting and removal.

It is understood that further embodiments may be conceived of, in which any configuration of balanced or unbalanced resonators, whether vibrating in transverse, longitudinal or torsional modes or any combination thereof, may be made isothermal by the foregoing means, and may be compensated for any minor thermal imbalance by means of either a thermal model of the resonator or the two-point temperature measurement method combined with algorithmic compensation to determine the unloaded resonant frequency. In alternative preferred embodiments, the enclosed resonator portions 10A or 10A' are at a closer average temperature to exposed resonator portions 10B or 10B' than required by the definition of "isothermal" found earlier in this application. In preferred embodiments the enclosed portion 10A or 10A' has an average temperature that is within 3° C., 2° C., 1° C., or 0.5° C. of exposed portions 10B or 10B', respectively, depending on the specific embodiment.

INDUSTRIAL APPLICABILITY

The present invention finds industrial applicability in the field of industrial machinery and more specifically, fluid property measurement devices.

While a number of exemplary aspects and embodiments have been discussed above, those possessed of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

The invention claimed is:

1. A method of measuring density of a target fluid, comprising the steps
   (a) providing a fluid density measurement device, including:
      (i) a housing, defining a chamber and an aperture;
      (ii) a resonator having length that is at least 5 times greater than its smallest diameter and having a longitudinal axis and nodal plane, transverse to said longitudinal axis, and that includes a tube having a first end and a second end and being closed at said second end by a second-end closure, and being attached to said housing at said nodal plane, which is sealingly joined to said aperture, blocking fluid ingress, and so that an enclosed resonator portion extends into said chamber and an exposed resonator portion extends outside of said chamber; and further including a drive rod centrally attached to said second-end closure and extending into said enclosed resonator portion;
      (iii) wherein said second-end closure includes a fluid end mass that would define a non-round shape on a plane cutting through said end mass transversely to said longitudinal axis and wherein said resonator is driven to vibrate torsionally about its longitudinal axis, and said target fluid is displaced by resultant rotational vibration of said end mass; and
      (iv) a transducer assembly; and
   (b) placing said exposed portion of said resonator in said target fluid;
   (c) placing and maintaining said resonator into an isothermal state;

(d) using said transducer assembly to excite said resonator such that said exposed resonator portion vibrates perpendicularly to a portion of its own surface and to sense resultant resonator vibrations; and (e) analyzing said resultant vibrations to determine density of said target fluid.

2. The method of claim 1, wherein said drive rod is in form of a tube.

3. The method of claim 1, wherein said fluid end mass defines a flat surface, extending in parallel to said longitudinal axis.

4. The method of claim 1, wherein at least one fin extends from said end mass, thereby causing more displacement of said target fluid by rotational vibration of said end mass.

5. The method of claim 4, wherein a plurality of fins extends from said end mass, said four fins being spaced equally about said end mass.

6. The method of claim 1 wherein said drive rod bears a magnet that together with a nearby electromagnet assembly mounted on said housing forms at least a part of said resonator exciting and sensing assembly.

7. The method of claim 1, wherein said housing is fluid impermeable and wherein both said housing and said exposed resonator portion are placed in said target fluid, so that said chamber and said enclosed resonator portion tend to assume the temperature of said target fluid and said exposed resonator portion, thereby placing and maintaining said resonator into an isothermal state.

8. The method of claim 1, wherein said housing is highly thermally insulating, causing said chamber to be adiabatic, so that said step of placing said exposed resonator portion into said target fluid causes said enclosed resonator portion to approach the temperature of said target fluid, thereby placing said resonator into an isothermal state.

9. The method of claim 1, wherein said measurement device further includes a temperature sensor located in said exposed resonator portion, and also further includes a temperature control element positioned to control temperature of said chamber and being responsive to said temperature sensor to control temperature of said chamber and thereby said enclosed resonator portion to equal that of said exposed resonator portion, so that said resonator is placed and maintained in an isothermal state.

10. The method of claim 1, wherein said tube extends into said chamber and is closed at its first end by a first end closure that includes an element of said transducer assembly.

11. The method of claim 10, wherein said element of said transducer assembly is a permanent magnet and wherein said transducer assembly further includes an electrical coil assembly, adapted to drive said permanent magnet and to sense its movement.

12. A fluid density measurement device, including:
(a) a housing, defining a chamber and an aperture;
(b) a resonator having length that is at least 4 times greater than its smallest diameter and having a longitudinal axis and nodal plane, transverse to said longitudinal axis, and that includes:
  (i) a tube having a first end and a second end;
  (ii) a second-end closure, closing said second end; and
(c) a drive rod centrally attached to said second-end closure and extending to said tube first end;
(d) a resonator transducer assembly;
(e) wherein said resonator is sealingly joined to said aperture at said nodal plane, blocking fluid ingress, and so that an enclosed resonator portion extends into said chamber and an exposed resonator portion extends outside of said chamber, and wherein said resonator transducer assembly drives said resonator such that said exposed resonator portion vibrates perpendicularly to a portion of its own surface; and
(f) wherein said measurement device further includes a temperature sensor located in said exposed resonator portion, and also further includes a temperature control element positioned to control temperature of said chamber and being responsive to said temperature sensor to control temperature of said chamber and thereby said enclosed resonator portion to equal that of said exposed resonator portion, so that said resonator is placed and maintained in an isothermal state.

13. The device of claim 12, wherein said housing is fluid impermeable and wherein both said housing and said exposed resonator portion are placed in said target fluid, so that said chamber and said enclosed resonator portion tend to assume the temperature of said target fluid and said exposed resonator portion, thereby further helping to place and maintaining said resonator into an isothermal state.

14. The device of claim 12, wherein said housing is highly thermally insulating, causing said chamber to be adiabatic, so that said step of placing said exposed resonator portion into said target fluid causes said enclosed resonator portion to approach the temperature of said target fluid, thereby further helping to place said resonator into an isothermal state.

15. The device of claim 12, wherein said tube extends into said chamber and is closed at its first end by a first end closure that includes an element of said transducer assembly.

16. The device of claim 15, wherein said element of said transducer assembly is a permanent magnet and wherein said transducer assembly further includes an electrical coil assembly, adapted to drive said permanent magnet and to sense its movement.

17. A method of measuring density of a target fluid, comprising the steps of:
(a) providing a fluid density measurement device, including:
  (i) a housing, defining a chamber and an aperture;
  (ii) a resonator having length that is at least 5 times greater than its smallest diameter and having a longitudinal axis and nodal plane, transverse to said longitudinal axis, and that includes a tube having a first end and a second end and being closed at said second end by a second-end closure, and being attached to said housing at said nodal plane, which is sealingly joined to said aperture, blocking fluid ingress, and so that an enclosed resonator portion extends into said chamber and an exposed resonator portion extends outside of said chamber; and further including a drive rod centrally attached to said second-end wall and extending into said enclosed resonator portion;
  (iii) a transducer assembly; and
  (iv) a first temperature measurement device in said enclosed portion and a second temperature measurement device in said exposed portion;
(b) placing said exposed portion of said resonator in said target fluid;
(c) using said transducer assembly to excite said resonator such that said exposed resonator portion vibrates perpendicularly to a portion of its own surface; and
(d) analyzing said resultant vibrations and said measurements of said first temperature sensor and said second temperature sensor to determine density of said target fluid.

18. A method of measuring density of a target fluid, comprising the steps
 (a) providing a fluid density measurement device, including:
  (i) a housing, defining a chamber and an aperture;
  (ii) a resonator having length that is at least 5 times greater than its smallest diameter and having a longitudinal axis and nodal plane, transverse to said longitudinal axis, and that includes a tube having a first end and a second end and being closed at said second end by a second-end closure, and being attached to said housing at said nodal plane, which is sealingly joined to said aperture, blocking fluid ingress, and so that an enclosed resonator portion extends into said chamber and an exposed resonator portion extends outside of said chamber; and further including a drive rod centrally attached to said second-end closure and extending into said enclosed resonator portion;
  (iii) a transducer assembly;
  (iv) a temperature sensor located in said exposed resonator portion; and
  (v) a temperature control element positioned to control temperature of said chamber and being responsive to said temperature sensor to control temperature of said chamber and thereby said enclosed resonator portion to equal that of said exposed resonator portion, so that said resonator is placed and maintained in an isothermal state; and
 (b) placing said exposed portion of said resonator in said target fluid;
 (c) placing and maintaining said resonator into an isothermal state;
 (d) using said transducer assembly to excite said resonator such that said exposed resonator portion vibrates perpendicularly to a portion of its own surface and to sense resultant resonator vibrations; and
 (e) analyzing said resultant vibrations to determine density of said target fluid.

* * * * *